United States Patent
Peyman

(10) Patent No.: US 6,342,051 B1
(45) Date of Patent: *Jan. 29, 2002

(54) TREATMENT OF ANOXIC TISSUE WITH ANGIOGENESIS-INDUCING IMPLANTS

(76) Inventor: Gholam A. Peyman, 8654 Pontchartrain Blvd., Apt. 1, New Orleans, LA (US) 70124

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/873,354

(22) Filed: Jun. 12, 1997

(51) Int. Cl.[7] .............................................. A61M 31/00
(52) U.S. Cl. ........................ 604/521; 623/4.1; 623/905
(58) Field of Search ................................ 623/1, 4, 1.42, 623/5.16, 6.62, 6.56, 905, 4.1; 604/60, 62, 49, 500, 521, 522

(56) References Cited

U.S. PATENT DOCUMENTS

| | | | |
|---|---|---|---|
| 4,778,787 A | 10/1988 | Catsimpoolas et al. | 514/25 |
| 4,795,423 A * | 1/1989 | Osterholm | 604/49 |
| 4,976,736 A * | 12/1990 | White et al. | 623/16 |
| 5,011,486 A * | 4/1991 | Aebischer et al. | 623/1 |
| 5,147,400 A * | 9/1992 | Kaplan et al. | 623/11 |
| 5,308,622 A * | 5/1994 | Casscells et al. | 424/422 |
| 5,397,356 A * | 3/1995 | Goble et al. | 623/13 |
| 5,443,950 A * | 8/1995 | Naughton et al. | 623/15 |
| 5,470,831 A * | 11/1995 | Whitman et al. | 514/16 |
| 5,545,208 A * | 8/1996 | Wolff et al. | 623/1 |
| 5,571,172 A * | 11/1996 | Chin | 623/1 |
| 5,710,175 A | 1/1998 | Nudelman et al. | 514/547 |
| 5,843,172 A * | 12/1998 | Yan | 623/1 |
| 5,849,034 A * | 12/1998 | Schwartz | 623/1 |
| 5,874,562 A | 2/1999 | Quertermous et al. | 536/23.5 |
| 5,905,146 A | 5/1999 | Lecka-Czernik | 536/23.5 |
| 5,941,868 A * | 8/1999 | Kaplan et al. | 604/500 |

OTHER PUBLICATIONS

"Vascular Endothelial Growth Factor Stimulates Schwann Cell Invasion and Neovascularization of Acellular Nerve Grafts", Sondell et al.; Brain Res, 11/99, 846(2), (Abstract only).
"Upregulation of Interleukin 8 by Oxygen–Deprived Cells in Glioblastoma Suggests a Role in Leukocyte Activation, Chemotaxis, and Angiogenesis", Desbaillets et al.; J Exp Med, 10/97, 186(8) (Abstract only).
"Outlook for the Future in the Treatment of Diabetic Retinopathy", Vialettes et al., Diabete Metab, 1994, 20(2 Pt 2), (Abstract only).
"A Possible Mechanism for Enhancement of Increased Production of Tumor Angiogenic Factor", Blumenson et al., Growth, Sep. 1976, 40 (3), (Abstract only).
"Immune Response and Neurotrophic Factor Interactions in Peripheral Nerve Implants", Gulati, Acta Haematol, 1998, 99(3), (Abstract only).
"Expression of Basic Fibroblast Growth Factor, Nerve Growth Factor, Platelet–Derived Growth Factor and Transforming Growth Factor–Beta in Human Brain Abcess", Liu et al., Acta Neuropathol, 1994, 88(2), (Abstract only).
Folkman, J. et al. "Angiogenesis", *J. Biol. Chem.* (1992) vol. 267, pp. 10931–10934.
Folkman, J., "Angiogenesis in cancer, vascular, rheumatoid and other disease." *Nat Med* (1995) vol. 1, pp. 27–31.

* cited by examiner

Primary Examiner—Paul B. Prebilic
(74) Attorney, Agent, or Firm—Roylance, Abrams, Berdo & Goodman, L.L.P.

(57) ABSTRACT

A method and implantable device for treating anoxic tissue. A substrate supporting an angiogenesis factor in an amount for treating anoxic tissue is implanted so as to promote revascularization of the tissue. The substrate is a physiologically compatible polymer and may have different configurations such as a fiber, a filament, a microsphere, a needle or a pin. The implantable device may be transported through a catheter or implanted directly in the anoxic tissue. The anoxic tissue may be heart, eye, brain, brain stem, spinal cord, bone and combinations of tissues.

13 Claims, 2 Drawing Sheets

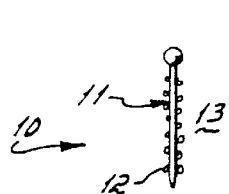
FIG. IA
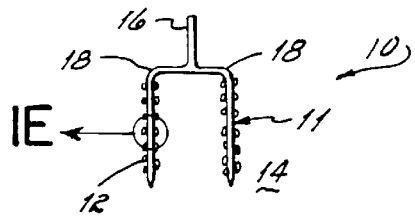
FIG. IB
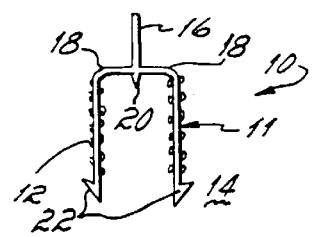
FIG. IC
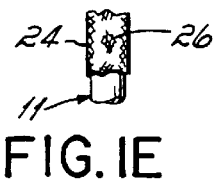
FIG. IE
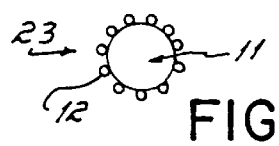
FIG. ID
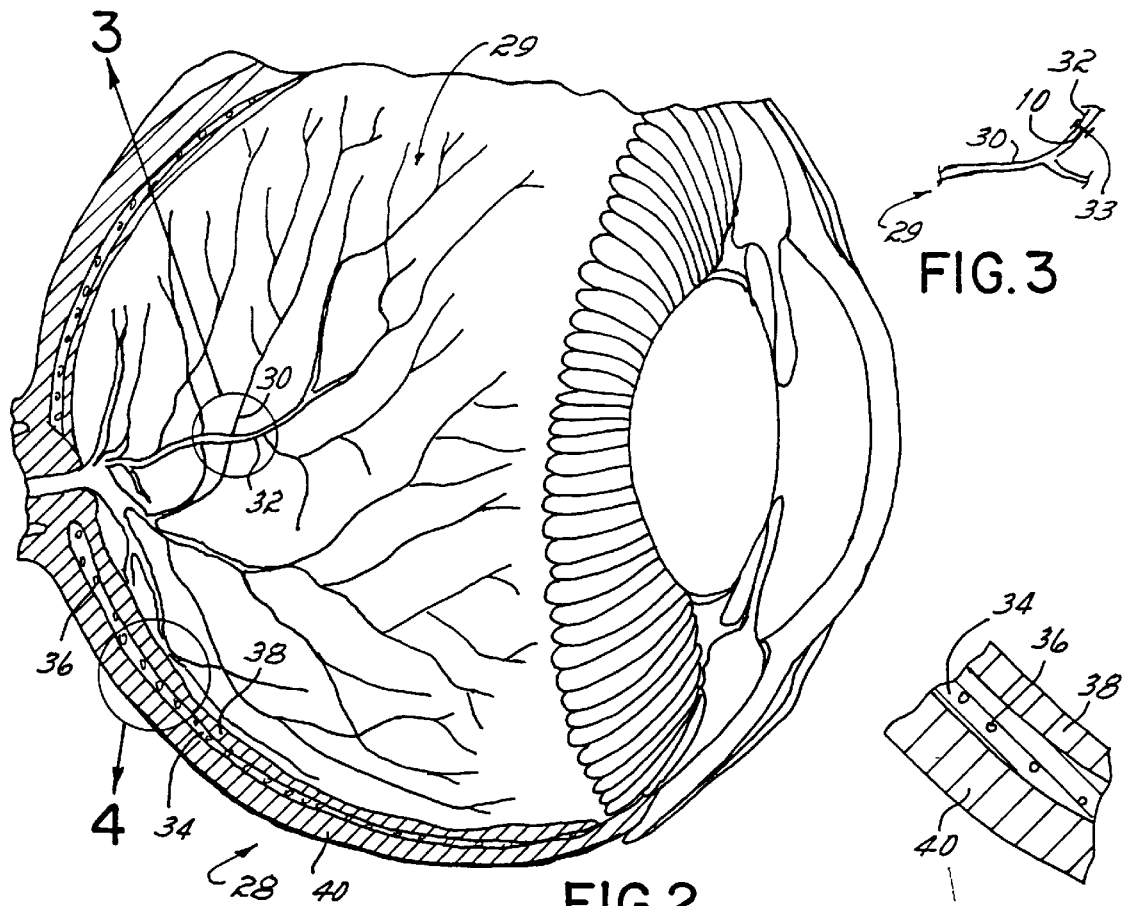
FIG. 2
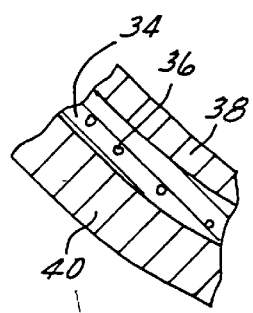
FIG. 3
FIG. 4
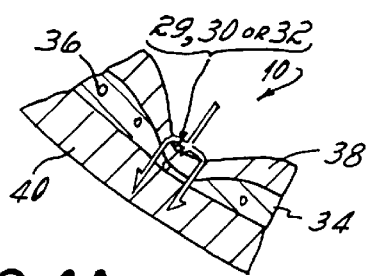
FIG. 4A
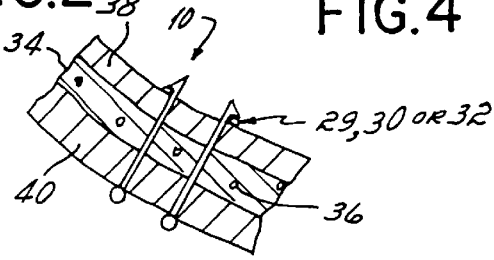
FIG. 4B

TREATMENT OF ANOXIC TISSUE WITH ANGIOGENESIS-INDUCING IMPLANTS

BACKGROUND OF THE INVENTION

Angiogenesis is the process of inducing new blood vessels. Angiogenesis-producing factors are signals that serve as stimuli to cause angiogenesis. The result of angiogenesis is neovascularization to initiate a blood supply to a tissue or to revascularize ischemic tissue. Neovascularization or revascularization by angiogenesis-producing factors includes recanalization whereby hollow capillary tubes form to support a blood supply.

Angiogenesis is also the process whereby a tissue responds to a tumor by inciting growth of new blood vessels toward the tumor. Beside tumors, substances that may induce angiogenesis include proteolytic enzymes, growth factors, and chemicals such as EDTA.

Proteolytic enzymes are secreted by tumor cells or destroyed cells in the process of cytolysis. These enzymes induce cell movement toward their chemical stimuli in the process of chemokinesis. Chemicals such as EDTA can cause instability of a cell membrane and similarly trigger cell movement. It has been also shown that growth factors, such as fibroblast growth factor (FGF), transforming growth factor (TGF), nerve growth factor (NGF), and so on, play a role in regulating proliferation of endothelial cells. Regardless of the pathogenesis of angiogenesis, the process is accompanied by proliferation of endothelial cells from initially normal vessels toward the stimulus.

Folkman in 1971 proposed the concept of anti-angiogenesis. Anti-angiogenesis involves inhibiting new blood vessel formation in order to either prevent growth of a tumor or control growth of metastatic tumors. Much work has been done in this area to identify and test anti-angiogenesis agents. Examples of such agents include anti-inflammatory or suppressive factors (inhibitors) that prevent endothelial cell proliferation, and inhibitors of proteolytic enzymes such as plasminogen activator inhibitors. Such inhibitors can prevent the breakdown of the protein matrix and maintain the integrity of endothelial cells, thereby preventing their migration. Efforts in this area have been concentrated in attempting to treat tumors by preventing neovascularization.

Although in the last two decades there have been attempts to revascularize an ischemic area of myocardial tissue using laser energy, these attempts have been only partially successful. This is due to laser-induced channels closing by themselves, as well as to the unpredictable rate of revascularization of these channels. Similarly, in central retinal vein thrombosis, attempts have been made to rupture small retinal veins with laser energy applied in a transpupillary direction, thus also rupturing Bruch's membrane in the hope of creating a channel from the retina to the choroidal circulation. These techniques have met with only minimal success; less than a 30% success rate has been achieved with this method to create new channels. Additionally, revascularization of the retina cannot occur in patients who have central vein occlusion or other diseases which create capillary occlusion in the retina or any other organ, such as the brain.

SUMMARY OF THE INVENTION

The present invention is directed to a method and device for treating anoxic tissue. A physiologically compatible device supports an angiogenesis factor in an amount for treating an anoxic tissue. The device is implanted in the anoxic tissue so as to induce revascularization of the tissue.

The invention is also directed to a method of making an angiogenesis-inducing implant, comprising supporting an angiogenesis factor on a physiologically compatible substrate for retaining the factor, to form an implantable device.

The invention also describes methods and materials used to successfully induce neovascularization in an ischemic tissue, in an attempt to reestablish function of these tissues. In particular embodiments, the devices and methods of the invention may be used to revascularize anoxic heart and eye tissue.

Until now, no attempt has been made to in fact use angiogenesis-stimulating factors to revascularize ischemic tissue. One example where angiogenesis-stimulating factors may be used is in a damaged heart muscle where closure of one or more coronary arteries has resulted in a myocardial infarction. Such closure leads to either acute myocardial infarction or to a gradual cardiomyopathy, with its predominant symptom of angina pectoris. Another example where angiogenesis-stimulating factors may be used is in anoxic tissue in the eye. Central retinal artery occlusion in the eye causes immediate discontinuation of blood supply to the retina. If this condition is not treated within a short period of time, or if the vessels are not reopened by themselves, pushing microemboli in the peripheral branches, complete loss of sight occurs. Another example is central vein occlusion that results from thrombosis of the central retinal vein. Lack of blood flow in the central retinal vein produces congestion, with subsequent breakdown of the capillary network and hemorrhage in the retinal tissue. Lack of oxygen and nutrients, carried by blood, produces ischemic processes in the retina and may result in the loss of sight.

Other advantages and embodiments will be understood with reference to the drawings and following detailed description.

BRIEF DESCRIPTION OF THE DRAWINGS

FIG. 1A is a device in the form of a single pin to be situated in the eye.

FIG. 1B is a device in the form of a fork-like pin to be situated in the eye.

FIG. 1C is a device in the form of a fork-like pin with arrowheads to be situated in the eye.

FIG. 1D is a device in the form of a microsphere to be situated in the heart.

FIG. 1E is one embodiment of the device shown in FIG. 1B showing a fiber coating on the fork-like pin to be situated in the eye.

FIG. 2 is a schematic longitudinal cross section of part of the human eye.

FIG. 3 is a fragmentary cross section of the circled area 3 of FIG. 2 showing a pin implanted along a vessel.

FIG. 4 is a fragmentary cross section of the circled area 4 of FIG. 2 showing an eye wall.

FIG. 4A is the section of the eye wall shown in FIG. 4 with a pin implanted from the interior.

FIG. 4B is a section of the eye wall shown in FIG. 4 with a pin implanted from the exterior.

DETAILED DESCRIPTION OF THE PREFERRED EMBODIMENT

Figure 5:
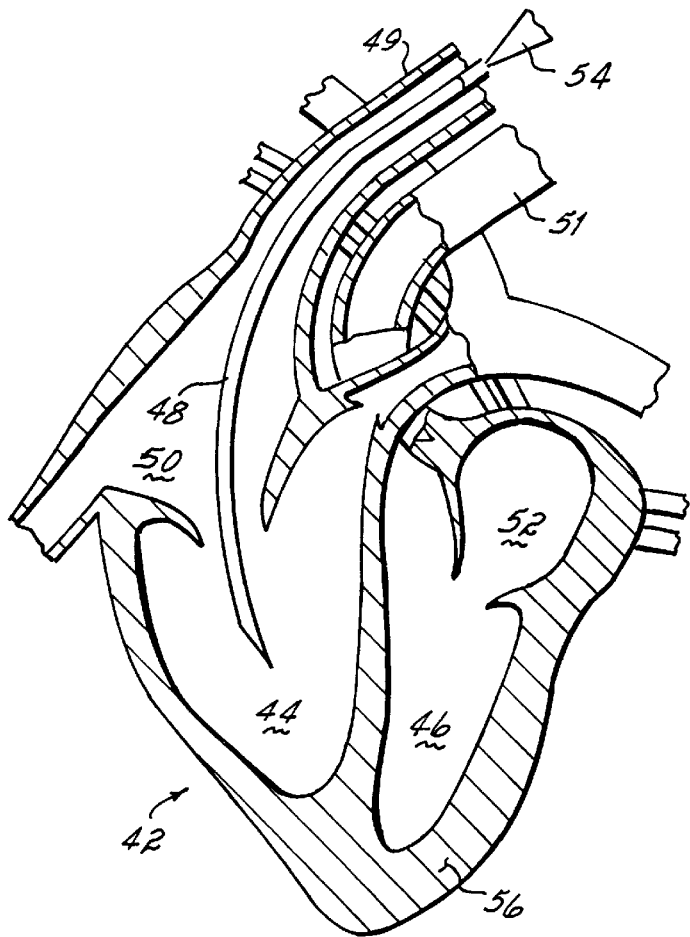
FIG. 5 is a schematic longitudinal cross section of the human heart.

As shown in FIGS. 1A–E the devices 10 of the present invention are physiologically compatible substrates 11 supporting angiogenesis-producing factors 12. The devices 10 may take various forms. As shown in FIG. 1A, the device 10 may be a single pin 13. The pin 13 may have a length of about 20 to about 4000 microns and a diameter of about 20 to about 1000 microns when used in organs such as heart and eye, but may extend up to many centimeters when implanted in larger organs and tissues, such as large bones. As shown in FIG. 1B, the device 10 may have a fork-like shape 14 with a head section 16 and two prongs 18. In one embodiment, the length of each prong is about 20 to about 5000 microns and the diameter is about 50 to about 1000 microns for use in organs such as heart and eye, but may be enlarged depending upon the size of the organ or tissue. In another embodiment, as shown in FIG. 1C, the device 10 has a substantially fork-like shape 14 with the head of the fork 16 extending between the prongs 18 and terminating in a complete arrowhead 20, and with each prong 18 of the fork 14 terminating in a one-sided arrowhead 22. In still another embodiment, as shown in FIG. 1D, the device 10 may be in the form of a microsphere 23, ranging in size from about 0.1 micron to about 3 microns. Other forms of the device are also possible, such as a ring form. As shown in FIG. 1E, any configuration of the device 10 may contain a coating 24 of fibers 26. The fibers 26 may be synthetic or natural fibers, such as silk, nylon, porous silicone, or other material.

The devices 10 support the angiogenesis-producing factors 12 by providing substrates 11, preferably biocompatible polymers, for retaining the factors 12. In one embodiment, the devices may be permeable. The devices may be manufactured of proteins, polyesters, polyamides, polyvinyl alcohol, polyolefins, polyanhydrides, or polycarboxylic acids. For example, proteins such as silk, hydroxyapatite, cross-linked or non-cross-linked collagen, cross-linked or non-cross-linked fibrin, catgut and mixtures of these proteins can be used. Polyesters such as polyethylene terephthalate, polycaprolactone, and mixtures of these polyesters can also be used. Similarly, a polyamide such as nylon or a polyvinyl alcohol may be used. Polyanhydrides such as poly(fatty acid dimer), poly(sebacic acid), and their copolymers of poly(fatty acid dimer-sebacic acid), and copolymers of bis(carboxyphenoxy)propane-sebacic acid may be used. Polycarboxylic acids such as polylactic acid, polyglycolic acid and mixtures of these may be used.

Polymeric substrates 11 configured into fibers or filaments and supporting angiogenesis-producing factors 12 can enhance the process of endothelial cell migration. One example of such a configuration is a polymeric device 10 containing silk and angiogenesis-producing factors 12. The polymeric device 10 can also be made of hydroxyapatite which subsequently can enhance neovascularization and ossification as needed; for example, in the bone or after evisceration in the eye.

The angiogenesis-producing factors 12 used in the present invention may be produced from proteolytic enzymes, cellular extracts, or destroyed cells. Other angiogenesis-producing factors 12 that may be used include fibrin growth factor (FGF), nerve growth factor (NGF), transforming growth factor (TGF), tumor necrosis factor (TNF), tissue plasminogen activator (TPA), urokinase, streptokinase, toxins, platelet factor 4 (PF4), suramin, ornithine decarboxylase, interleukins (IL), SPARC platelet activating factors (PAF), prostaglandins, phorbols, lipopolysaccharides, and thrombin.

Polymeric devices 10 coated with angiogenesis factors 12 induce neovascular tissue to form and to move from a normal unaffected area of the tissue toward an ischemic area. FIG. 2 shows a human eye 28 which may become anoxic in a particular area due to lack of blood supply through a blood vessel 29 such as the retinal artery 30 or retinal vein 32. As shown in FIG. 3, for revascularization in the case of central vein thrombosis of the eye 28, a regular pars plana vectrectomy is performed with incisions 33 made along a vessel 29. The vitreous is removed by a vitrector under direct visualization. The small branches of the central retinal vein 32 are isolated, and small incisions 33 are made adjacent to them to free them from the surrounding structure. The implanted devices 10 depress the branches of the retinal vein 32, forcing the branches down into the choroid tissue 34 where they are held by the force exerted by the solid polymer substrate 11 portion of the device 10. The choroidal vessels 36, in turn, penetrate and migrate into this structure and simultaneously create new channels from the choroid tissue 34 into the branches of the retinal vein 32. FIG. 4A shows the device 10 depressing a key vessel 29, 30, 32 into the choroid tissue 34, where the device 10 is implanted from the inside. FIG. 4B shows the device 10 after implantation from the outside. Similarly, in an anoxic area of the retina 38, multiple devices 10 coated with angiogenesis-producing factors 12 may be implanted through the retina 38 in the choroid 34 to induce migration and recanalization of the retina 38.

Implanting the devices 10 can be performed not only transvitrially, but also from outside the eye 28 through the sclera 40 to create neovascularization at the desired site. Furthermore, in early cases of central retinal artery 30 occlusion or branch retinal artery occlusion, recanalization may be achieved using the methods and devices 10 of the invention.

As shown in FIG. 5, a human heart 42 having areas of anoxia in the right ventricle 44 and left ventricle 46 may be treated by the methods and devices 10 of the present invention. To administer the devices 10 to the anoxic ventricular 44,46 areas of the heart 42, the devices 10 may be transported to the heart 42 by a catheter 48.

The catheter 48 is inserted through any accessible venous structure lying in the subcutaneous tissue, such as the anticubital vein or femoral vein. The catheter 48 is advanced toward the vena cava 49 and is subsequently brought through the right atrium 50 and into the right ventricle 44 of the heart 42. Similarly, if a catheter 48 is moved through the arterial system, such as the femoral artery or anticubital artery, the catheter 48 is brought through the aorta 51 to the left atrium 52 to gain access to the left ventricle 46. These techniques are routinely used to either perform angiography or for balloon angioplasty, such as when a coronary artery is reached via the aorta 51. In one embodiment of the present invention, a laser 54 is connected to a catheter 48 to either unblock the coronary artery or to create small channels in the myocardium 56 from inside the heart 42 in the process of recanalization.

Figure 5A:
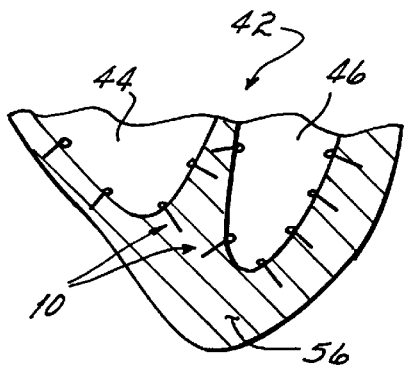
FIG. 5A is a fragmentary cross section of the heart shown in FIG. 1 showing one embodiment of the device in the form of pins implanted from inside a wall of the heart.
Figure 5B:
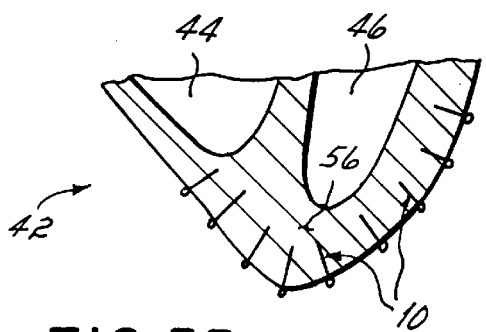
FIG. 5B is a section of the heart shown in FIG. 5 showing one embodiment of the device in the form of pins implanted from outside a wall of the heart.
Figure 5C:
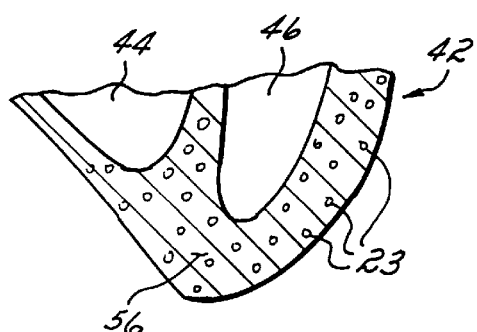
FIG. 5C is a section of the heart shown in FIG. 5 showing another embodiment of the device in the form of microspheres placed in a wall of the heart.

The devices 10 may be injected into the heart 42 by force, or may be mechanically implanted into the heart 42. The devices 10 may be configured into a needle-like or pin-like shape for easier penetration, or may be configured as a fiber, filament, or microsphere 23. As shown in FIG. 5A, the device 10 in the form of a pin 13 can be implanted from inside the wall of the heart 42, that is, into the myocardium 56. As shown in FIG. 5B, the device 10 in the form of a pin 13 may also be implanted from outside the heart 42 into the wall of the myocardium 56. As shown in FIG. 5C, the device 10, in the form of a microsphere 23, may be placed in the myocardium 56 either from inside or outside the heart 42.

Depending on the anoxic area and extent of the anoxic process in a tissue, the devices 10 may be placed at regular intervals to enhance vascularization of the entire ischemic area. The devices 10 may be implanted as close as a few millimeters or as far as a few centimeters from each other, depending on the need for vascularization. The process can be repeated, if desired, through a small incision made in the chest wall. The devices 10, and methods of using the devices 10 disclosed in the present invention, can also be used in other parts of the body where vascular occlusion has occurred or is threatening to occur. Such occlusion may be the result of, for example, closure of the main vessels thereby affecting the brain, brain stem, or spinal cord. The methods and devices 10 of the present invention may also find use after a spinal cord injury. Revascularization and recanalization may also have some application in the extremities where major vessels may be impaired, for example, as a result of arteriosclerosis, an inflammatory process, or trauma.

Other variations or embodiments of this invention will become apparent to one of ordinary skill in the art in view of the above drawings and description, and the forgoing embodiments are not to be construed as limiting the scope of this invention.

What is claimed is:

1. A method of inducing revascularization of anoxic or ischemic tissue in an occluded retinal vessel or artery in an eye, said method comprising:

making an incision in the occluded blood vessel or artery adjacent the occlusion; and implanting an implantable device in said blood vessel or artery to depress said blood vessel or artery against tissue adjacent the occlusion to release an angiogenesis factor and to induce revascularization of the tissue, said implantable device comprising a substrate and an angiogenesis factor in an amount sufficient to induce revascularization of and occluded blood vessel or artery.

2. The method of claim 1, wherein said blood vessel is a retinal vein.

3. The method of claim 1, wherein said tissue adjacent the occlusion is choroid tissue and said method comprises forcing said retinal vessel or artery into said choroid tissue and retaining said retinal vessel or artery in place by said implantable device.

4. A method of inducing revascularization of anoxic or ischemic tissue in an occluded retinal blood vessel, said method comprising:

implanting an implantable device through the retina in the eye into an anoxic or ischemic area of said retinal blood vessel and forcing the retinal blood vessel against choroidal tissue in the eye, said implantable device having a substrate and an angiogenesis factor in an amount sufficient to induce revascularization of a retinal blood vessel; and releasing the angiogenesis factor from said implantable device to said retinal blood vessel to induce revascularization from the choroidal tissue to the retinal blood vessel.

5. The method of claim 1, wherein said implantable device is a pin having a point for penetrating the anoxic or ischemic tissue and having a coating of said angiogenesis factor.

6. The method of claim 1, wherein said implantable device is a pin having a length of about 20 to about 4000 microns, and said method comprises penetrating said retinal vessel or artery with said pin.

7. The method of claim 1, wherein said implantable device has a pair of prongs, with a length of about 20 to 5000 microns, and said method comprises penetrating said retinal vessel or artery with said prongs.

8. The method of claim 7 wherein said prongs include a hook for retaining the device in the tissue.

9. The method of claim 1, wherein said angiogenesis factors are produced from proteolytic enzymes, cellular extracts or destroyed cells.

10. The method of claim 1, wherein said implantable device is a pin and said method comprises penetrating said occluded blood vessel.

11. The method of claim 1, wherein said implantable device includes a pair of prongs, each prong having a hook, and said process comprises penetrating said occluded blood vessel with said device and depressing said occluded blood vessel.

12. The method of claim 1, wherein said implantable device is a pin and said method comprises inserting said pin into the retina from inside the eye.

13. The method of claim 1, wherein said implantable device is a pin and said method comprises inserting said pin through the outer surface of the eye into the retina.

* * * * *